(12) United States Patent
Ahmad et al.

(10) Patent No.: US 9,795,758 B2
(45) Date of Patent: Oct. 24, 2017

(54) VENTILATOR WITH INTEGRATED COOLING SYSTEM

(71) Applicant: Breathe Technologies, Inc., Irvine, CA (US)

(72) Inventors: Samir S. Ahmad, San Diego, CA (US); Mark J. Zechmeister, Costa Mesa, CA (US); Enrico Brambilla, Irvine, CA (US)

(73) Assignee: Breathe Technologies, Inc., Irvine, CA (US)

( * ) Notice: Subject to any disclaimer, the term of this patent is extended or adjusted under 35 U.S.C. 154(b) by 625 days.

(21) Appl. No.: 13/927,016

(22) Filed: Jun. 25, 2013

(65) Prior Publication Data

US 2014/0373842 A1 Dec. 25, 2014

(51) Int. Cl.
*A62B 7/00* (2006.01)
*A61M 16/10* (2006.01)
(Continued)

(52) U.S. Cl.
CPC .... *A61M 16/1075* (2013.01); *A61M 16/0051* (2013.01); *A61M 16/0672* (2014.02);
(Continued)

(58) Field of Classification Search
CPC ...... A61M 16/0627; A61M 2205/3606; A61M 2205/3673; A61M 16/0078;
(Continued)

(56) References Cited

U.S. PATENT DOCUMENTS

| 1,913,347 A | 6/1933 | Taylor |
| 2,104,589 A | 1/1938 | Hartman |

(Continued)

FOREIGN PATENT DOCUMENTS

| CN | 201919784 | 8/2011 |
| JP | 2011206556 | 10/2011 |

(Continued)

OTHER PUBLICATIONS

International Search Report and Written Opinion for International Application No. PCT/US14/43713, dated Nov. 14, 2014, 10 Pages.

*Primary Examiner* — Todd J Scherbel
*Assistant Examiner* — Victoria Murphy
(74) *Attorney, Agent, or Firm* — Stetina Brunda Garred and Brucker; Mark B. Garred

(57) ABSTRACT

A ventilation gas cooling apparatus is configured in a modular form adapted for selective removable engagement to a ventilator. The apparatus includes a gas inlet port, a gas delivery port, a pressure sensing port, and a thermoelectric cooler. The inlet port is fluidly connectible to a source of therapeutic breathing gas at an external end and is fluidly connectible to an inlet of the ventilator at an internal end. The delivery port is fluidly connectible to a patient circuit at an external end and is fluidly connectable to an outlet of the ventilator at an internal end. The pressure sensing port is fluidly connectible to both a pressure sensing port of the ventilator and to the patient circuit. The apparatus may further include a cooling fluid system operative to circulate either a gas or liquid coolant along at least a portion of a multi-lumen tube integrated into the patient circuit.

15 Claims, 8 Drawing Sheets

(51) Int. Cl.
  *A61M 16/06* (2006.01)
  *A61M 16/00* (2006.01)
(52) U.S. Cl.
  CPC ..... *A61M 16/0057* (2013.01); *A61M 16/0627* (2014.02); *A61M 16/0666* (2013.01); *A61M 2016/0027* (2013.01); *A61M 2205/3606* (2013.01); *A61M 2205/502* (2013.01)
(58) Field of Classification Search
  CPC .......... A61M 16/0075; A61M 16/1075; A61M 16/1045; A61M 1/369; A61M 5/44; A61M 2021/066; A62M 16/06; A62B 9/003; A62B 17/005
  USPC ........................................ 128/204.15, 204.16
  See application file for complete search history.

(56) References Cited

U.S. PATENT DOCUMENTS

| | | | |
|---|---|---|---|
| 2,190,613 A | 2/1940 | Sittler | |
| 2,418,473 A | 4/1947 | Lambertsen et al. | |
| 5,487,380 A * | 1/1996 | Grabenkort | A61M 16/22 128/204.15 |
| 5,662,161 A | 9/1997 | Hughes et al. | |
| 5,697,361 A | 12/1997 | Smith | |
| 5,925,831 A * | 7/1999 | Storsved | A61B 5/087 128/204.23 |
| 6,382,208 B2 * | 5/2002 | Reedy | A62B 9/003 128/204.17 |
| 6,523,538 B1 * | 2/2003 | Wikefeldt | A61M 16/01 128/204.18 |
| 6,571,574 B1 | 6/2003 | Blackstone | |
| 6,792,623 B2 | 9/2004 | Luppi | |
| 6,983,749 B2 | 1/2006 | Kumar et al. | |
| 7,203,063 B2 * | 4/2007 | Bash | G06F 1/20 165/104.33 |
| 7,525,663 B2 * | 4/2009 | Kwok | A61M 16/16 128/203.27 |
| 7,674,281 B2 | 3/2010 | Worm | |
| 7,938,523 B2 * | 5/2011 | Aldrich | B41J 2/17513 347/84 |
| 8,230,852 B2 | 7/2012 | Zhang et al. | |
| 2007/0113847 A1 | 5/2007 | Acker et al. | |
| 2010/0224194 A1 | 9/2010 | Walker et al. | |
| 2011/0197885 A1 * | 8/2011 | Wondka | A61B 5/03 128/204.22 |
| 2012/0138050 A1 | 6/2012 | Wondka et al. | |

FOREIGN PATENT DOCUMENTS

| | | |
|---|---|---|
| WO | WO2011058371 | 5/2011 |
| WO | WO2013061288 | 5/2013 |

* cited by examiner

VENTILATOR WITH INTEGRATED COOLING SYSTEM

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

1. Technical Field of the Invention

The present disclosure relates generally to patient ventilation systems, and more particularly to a ventilation system incorporating a cooling device which is uniquely configured to provide cooled air to a patient receiving artificial ventilation.

2. Description of the Related Art

The respiration system of the human body provides needed oxygen intake, oxygen/carbon dioxide exchange, and carbon dioxide expulsion functions, each of which involves the lungs. In this regard, the lungs function as a gas-exchanging organ in which inhaled oxygen is passed to the blood, and collected carbon dioxide is passed from the blood to the air. Additionally, the lungs function as a respiratory pump that transports oxygen-rich air into the lungs, and the carbon dioxide-rich air out of the lungs. The breathing center in the brain, central and peripheral nerves, the osseous thorax and the breathing musculature as well as free, stable respiratory paths are necessary for a correct functioning of the respiratory pump.

With patients suffering from certain diseases or other serious medical conditions, there is a constant overload on or exhaustion of the respiratory pump. A typical syndrome is pulmonary emphysema with flat-standing diaphragms without the ability to contract, and the respiratory paths are usually extremely slack and tend to collapse. Consequentially, the patient experiences difficulty with breathing deeply enough and providing the body with needed oxygen while also expelling waste carbon dioxide.

The use of ventilator and breathing circuits to provide respiratory assistance to a patient is well known in the medical arts. The ventilator and breathing circuit provides mechanical assistance to patients who are having difficulty breathing on their own. In certain types of breathing circuits, a ventilator unit or flow generator is fluidly connected to a ventilation mask worn by the patient. Such fluid connection is typically achieved through the use of ventilation tubing or a tubing circuit which is operative to deliver the ventilation gas from the flow generator to the patient via the mask worn by the patient.

Oftentimes to prevent additional damage to the patient it is beneficial to facilitate a reduction in the body temperature of the patient. For example, it is known that a patient experiencing myocardial infarction tends to have an extremely elevated body temperature that often times leads to tissue damage. As such, in certain circumstances it would be beneficial to lower the temperature of the patient's body. It is known that filling the lungs with cooled air will reduce the overall body temperature of the patient via heat exchange with the blood circulating into and out of the lungs. Accordingly, there is a need in the art for a ventilation system that provides cooled air to the patient.

BRIEF SUMMARY OF THE INVENTION

In accordance with the present disclosure there is provided a ventilation gas cooling apparatus which, in an exemplary embodiment, is configured in a modular form adapted for selective removable engagement to a ventilator. The cooling apparatus or unit includes a gas inlet port, a gas delivery port, a pressure sensing port, and a thermoelectric cooler. The inlet port is fluidly connectible to a source of therapeutic breathing gas at an external end and is fluidly connectible to an inlet of the ventilator at an internal end. The delivery port is fluidly connectible to a patient circuit at an external end and is fluidly connectable to an outlet of the ventilator at an internal end. The pressure sensing port is fluidly connectible to both a pressure sensing port of the ventilator and to the patient circuit. The thermoelectric cooler of the cooling unit is preferably a Peltier cell disposed between a cooling plate which absorbs heat and a heat sink which dissipates heat. The cooling plate is situated so as to be adjacent to the delivery port. In the cooling unit, a fan is preferably cooperatively engaged to the heat sink of the thermoelectric cooler to assist in the dissipation of heat therefrom.

The cooling unit may be physically connected to the ventilator, such that the inlet port is directly attached to the ventilator inlet, and the delivery port is directly attached to the ventilator outlet. Alternatively, the cooling unit may be pneumatically connected to the ventilator, such that the inlet port fluidly communicates with the ventilator inlet via a portion of the patient circuit, and the delivery port fluidly communicates with the ventilator outlet via a portion of the patient circuit.

In certain embodiments, the inlet port may further include a pressurized inlet chamber, to allow for cooling of the incoming air. The delivery port may follow a serpentine pattern to maximize contact surface with the thermoelectric cooler.

The cooling unit may further include a cooling fluid system which is operative to circulate either a gas coolant or a liquid coolant along at least a portion of a multi-lumen tube which is integrated into the patient circuit. In one embodiment of the cooling fluid system, the cooling unit is outfitted with a cooling fluid send port which is fluidly connectable to a cooling fluid send lumen of the multi-lumen tube integrated into the patient circuit. In this embodiment, the preferred cooling fluid is a gas coolant which flows from the cooling fluid send port of the cooling unit, through the cooling fluid send lumen of the multi-lumen tube, and is ultimately vented to ambient air at the patient interface. It is contemplated that the cooling fluid send port in this embodiment (wherein the cooling fluid is a gas coolant) may be in fluid communication with the outlet port of the cooling unit. In another embodiment of the cooling fluid system, the cooling unit may further include a cooling fluid return port which is fluidly connectable to a cooling fluid return lumen of the multi-lumen tube integrated into the patient circuit. In this embodiment wherein the cooling fluid send and return lumen's of the multi-lumen tube are fluidly connectable to respective ones of the cooling fluid send and return ports of the cooling unit, the cooling fluid is preferably a liquid coolant circulated through the multi-lumen tube in a closed loop system.

The circulation of the cooling fluid through the multi-lumen tube in accordance with either of the aforementioned embodiments of the cooling fluid system is preferably facilitated by a cooling fluid pump of the cooling unit which is positioned adjacent to the cooling plate of the thermoelectric cooler thereof. A preferred patient interface is preferably a mask such as a nasal pillows mask. If the patient interface is a nasal pillows mask, it is contemplated that such mask will be specifically configured to create a jet venturi of the ventilation gas flowing therein, thereby in entraining ambient air in the patient's circuit and minimizing or reducing leakage therefrom. An alternative patient interface may comprise a helmet interface.

The present invention is best understood by reference to the following detailed description when read in conjunction with the accompanying drawings.

BRIEF DESCRIPTION OF THE DRAWINGS

These, as well as other features of the present invention will become more apparent upon references to the drawings wherein.

Common reference numerals are used throughout the drawings and the detailed description to indicate the same elements.

DETAILED DESCRIPTION OF THE INVENTION

The detailed description set forth below in connection with the appended drawings is intended as a description of the several presently contemplated embodiments of a ventilator with an integrated cooling system. The system delivers breathing gas to a patient for respiratory assistance, wherein the breathing gas has been pre-cooled before arriving at the patient. Though a typical breathing gas is air, it is contemplated that such breathing gas may also be oxygen with air, heliox, or other therapeutic gas mixtures. This description is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
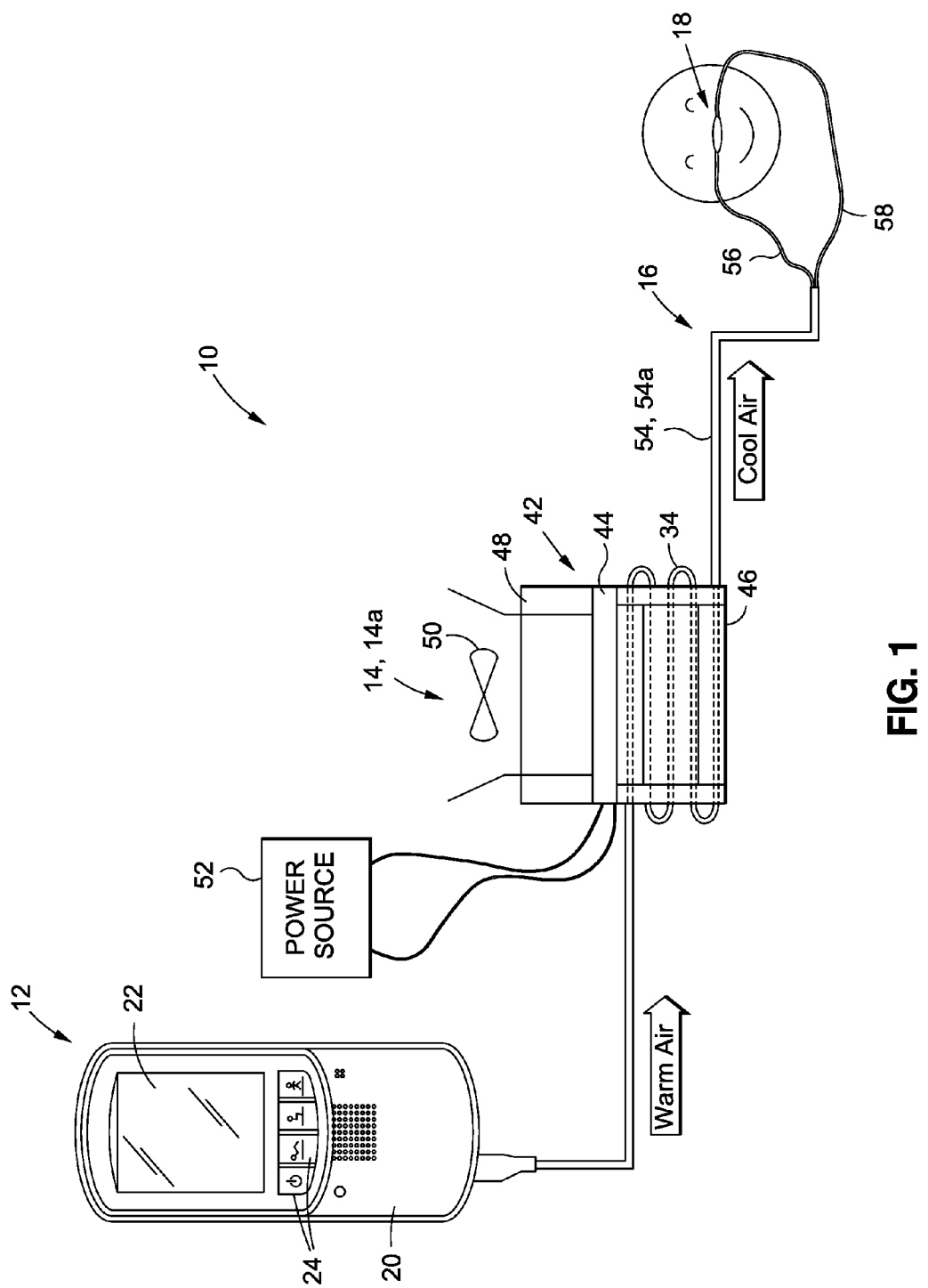
FIG. 1 is a block diagram showing the components of a ventilator apparatus in accordance with various embodiments of the present disclosure, including a ventilator, patient interface, cooling apparatus, and patient circuit.

Referring to the block diagram of FIG. 1, one embodiment of a ventilation system 10 is generally comprised of a ventilator 12, a cooling unit 14, patient circuit 16 and a patient interface 18. The patient interface 18 may include such devices as a full-face mask or a nasal mask that can be placed in direct gas flow or pneumatic communication with the upper respiratory tract of a patient, i.e., the nasal cavity and/or the oral cavity. It will be appreciated that other apparatuses that so interface the respiratory system of the patient to the ventilator 12, either non-invasively or invasively, may be substituted without departing from the scope of the present disclosure, so long as certain features noted below are incorporated therein. In the ventilation system 10, a preferred patient interface 18 is a nasal pillows mask, such as that described in Applicant's U.S. patent application Ser. No. 12/753,856 entitled Methods, Systems and Devices for Non-Invasive Open Ventilation for Treating Airway Obstructions filed Apr. 2, 2010, the disclosure of which is incorporated herein by reference. In the '856 Application, one embodiment of a nasal pillows mask is configured to create a jet venturi of the ventilation gas flowing therein, thereby in entraining ambient air in a manner minimizing leakage from the patient circuit, as may provide certain advantages in relation to the functionality of the exemplary ventilation system 10. A potential alternative patient interface 18 is a CPAP helmet, such as the CaStar helmet produced by StarMed Medical Disposables.

Figure 2:
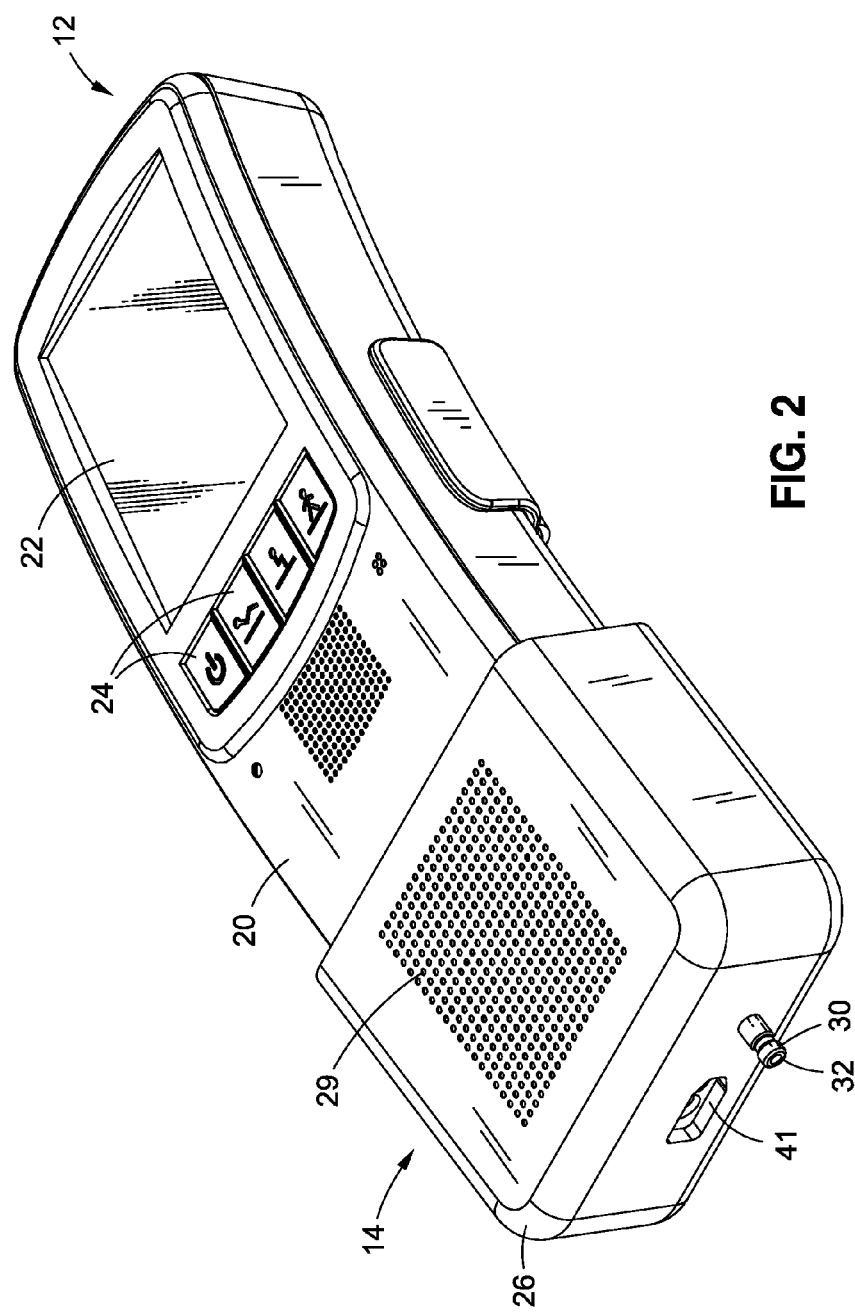
FIG. 2 is a perspective view illustrating the cooling unit of the present invention as cooperatively engaged to a ventilator.

In the exemplary embodiment shown in FIGS. 1 and 2, the ventilator 12 comprises a generally quadrangular housing 20 having a display 22 integrated into the top surface thereof. Also integrated into the housing 20 are a plurality of control buttons 24 which extend along one side of the display 22. Though not shown with particularity in FIGS. 1 and 2, the ventilator 12 further comprises an inlet port, an outlet port and a pressure sensing port which extend to a common peripheral side surface of the housing 20. The outlet port of the ventilator 12 is used to facilitate the flow of pressurized air therefrom, with the inlet port being used to facilitate the flow or delivery of air or another suitable therapeutic fluid therein. The pressure sensing port is used for reasons which will be described in more detail below.

In the ventilation system 10, the ventilator 12 is preferably outfitted with the cooling unit 14. The cooling unit 14 is preferably a modular component, capable of selective retrofit application to the ventilator 12. More particularly, due to the structural features of the cooling unit 14 as will be described in more detail below, the same is capable of being releasably attached to the ventilator 12. As will also be discussed in more detail below, the cooling unit 14, if cooperatively engaged to the ventilator 12, is operative to facilitate the cooling of pressurized air flowing from the exhaust outlet port of the ventilator 12 into the patient circuit 16 and ultimately to the patient interface 18 worn by a patient.

Figure 3:
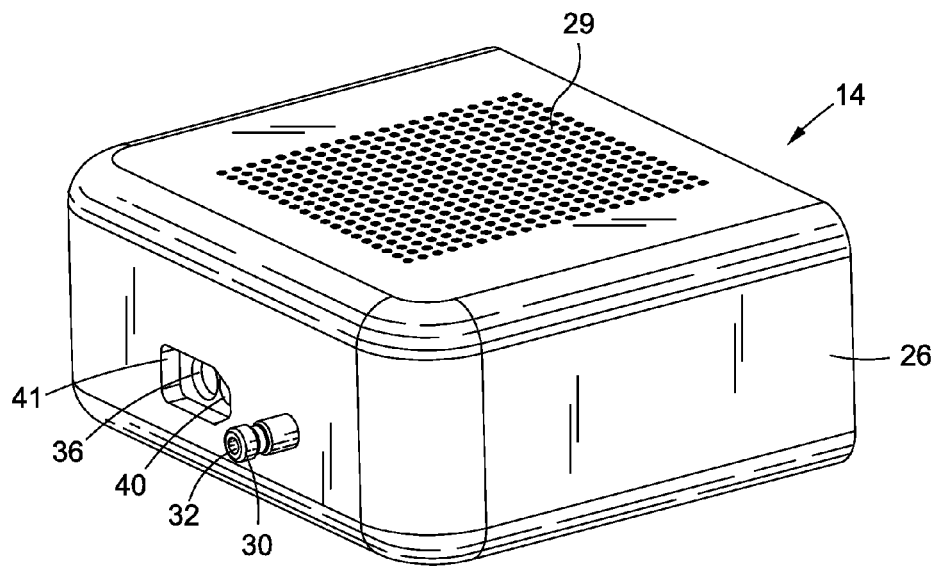
FIG. 3 is a perspective view of the cooling unit of the present invention.
Figure 4:
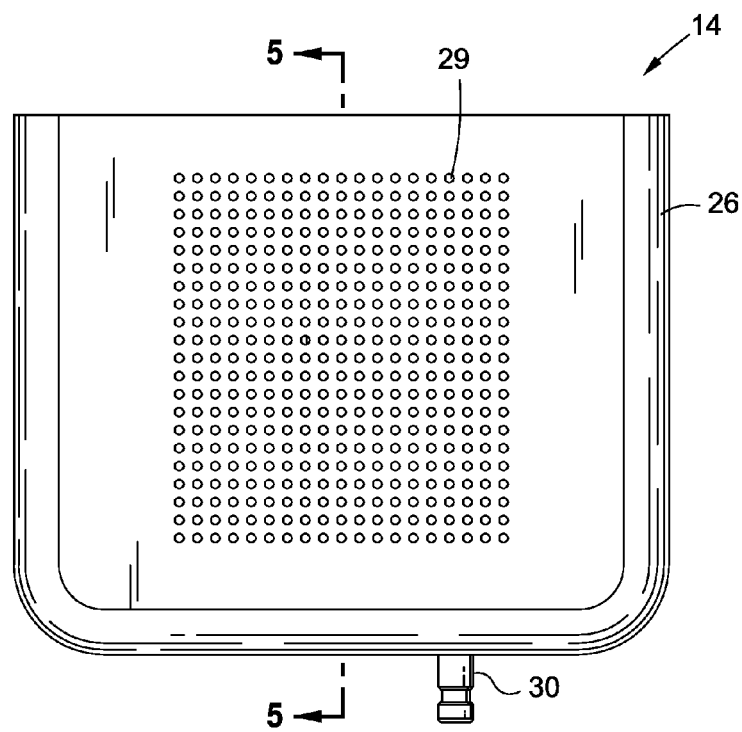
FIG. 4 is a font elevational view of the cooling unit of the present invention.

As is shown in FIGS. 2-9, the cooling unit 14 comprises a housing 26 which has a generally quadrangular configuration. The housing 26 defines a recess or receptacle 28 within one of the peripheral side surfaces thereof. As is best seen in FIG. 2, the receptacle 28 is sized and configured to be complementary to and to accommodate a portion of the housing 20 of the ventilator 12. As is seen in FIGS. 3 and 4, formed within the top surface of the housing 26 is a cooling grill 29, the use of which will be described in more detail below.

Figure 5:
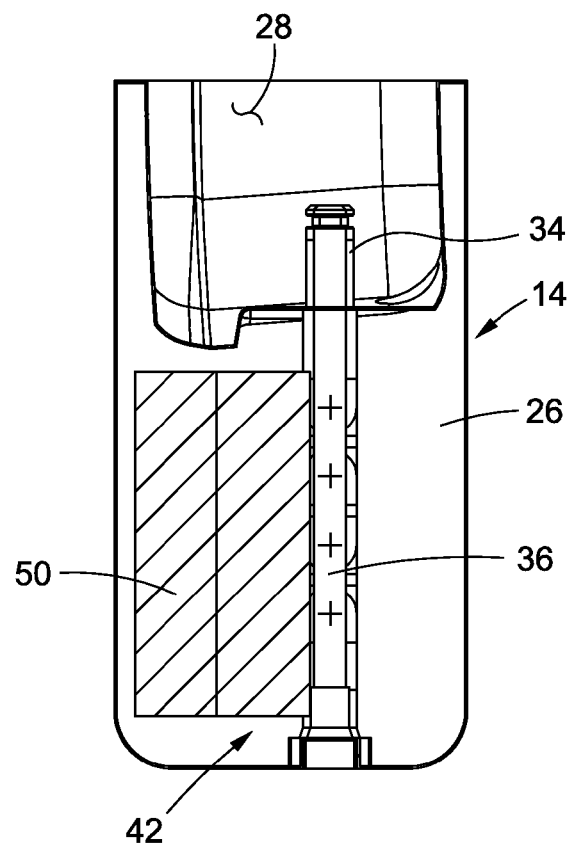
FIG. 5 is a cross-sectional view taken along line 5-5 of FIG. 4.
Figure 6:
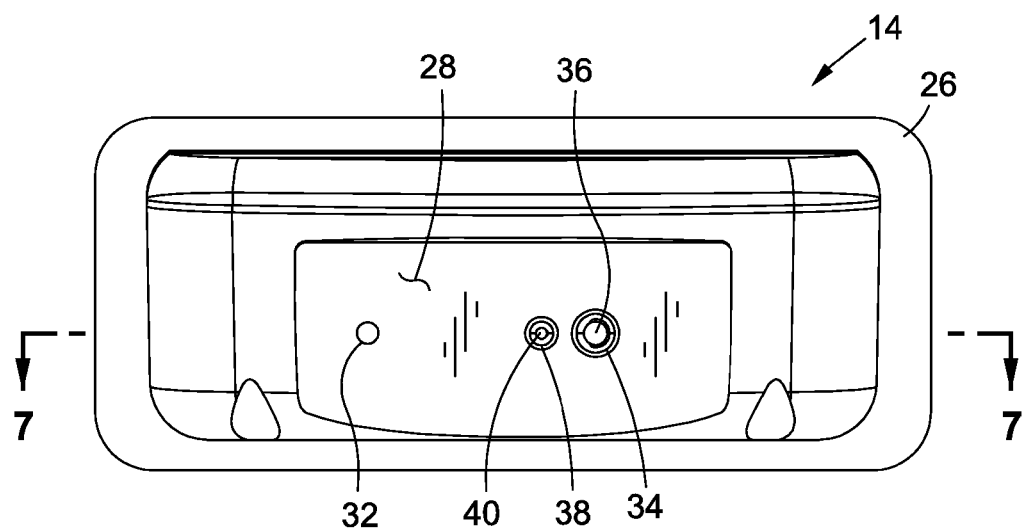
FIG. 6 is a top elevational view of the cooling unit shown in F FIG. 4.
Figure 7:
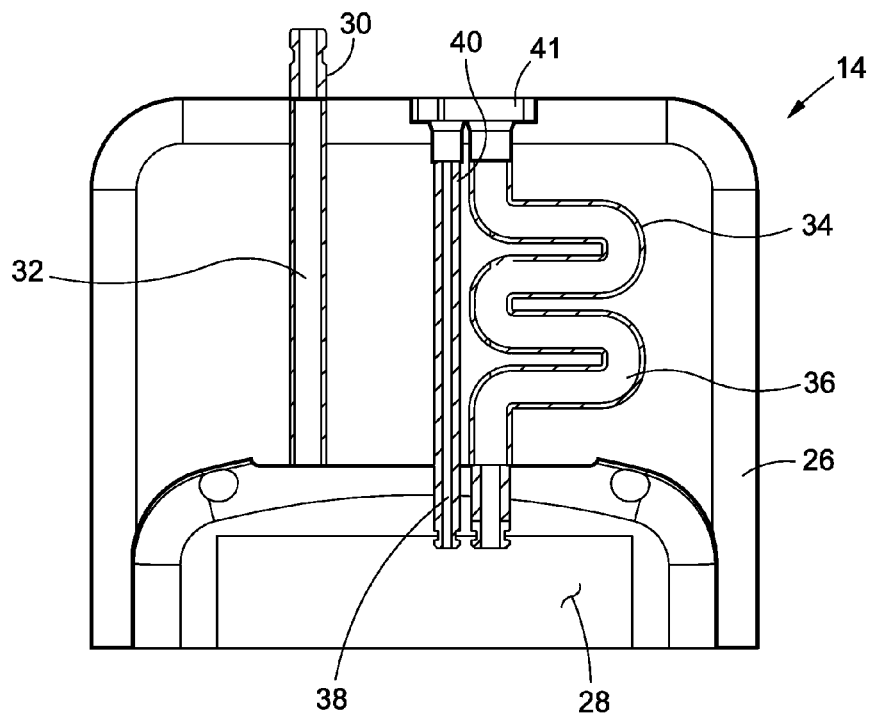
FIG. 7 is a cross-sectional view taken along line 7-7 of FIG. 6.

Referring now to FIGS. 5-7, the cooling unit 14 further comprises an elongate, linear gas inlet port 30, the majority of the length of which is disposed within the interior of the housing 26. The inlet port 30 has a tubular configuration with one end thereof extending to the receptacle 28 and the opposite end thereof protruding from that peripheral side surface of the housing 26 opposite that including the receptacle 28 formed therein. Along these lines, the gas inlet port 30 defines an inlet lumen 32 which fluidly communicates with ambient air and with the interior of the receptacle 28 when the cooling unit 14 is not cooperatively engaged to the ventilator 12.

In addition to the gas inlet port 30, the cooling unit 14 comprises an elongate gas delivery port, the majority of the length of which is also disposed within the interior of the housing 26. The gas delivery port 34 has a tubular, serpentine configuration with one end thereof extending into the receptacle 28 and the opposite end thereof extending to and terminating at that peripheral side surface of the housing 26 having a portion of the gas inlet port 30 protruding therefrom. As such, like the gas inlet port 30, the gas delivery port 34 defines a delivery lumen 36 which fluidly communicates with ambient air and with the interior of the receptacle 28 when the cooling unit is not cooperatively engaged to the ventilator 12. The serpentine configuration of the delivery port 34 is used to increase the effective length of the delivery lumen 36, and hence the travel path of air or another fluid flowing therethrough, for reasons which will be discussed in more detail below.

Figure 8:
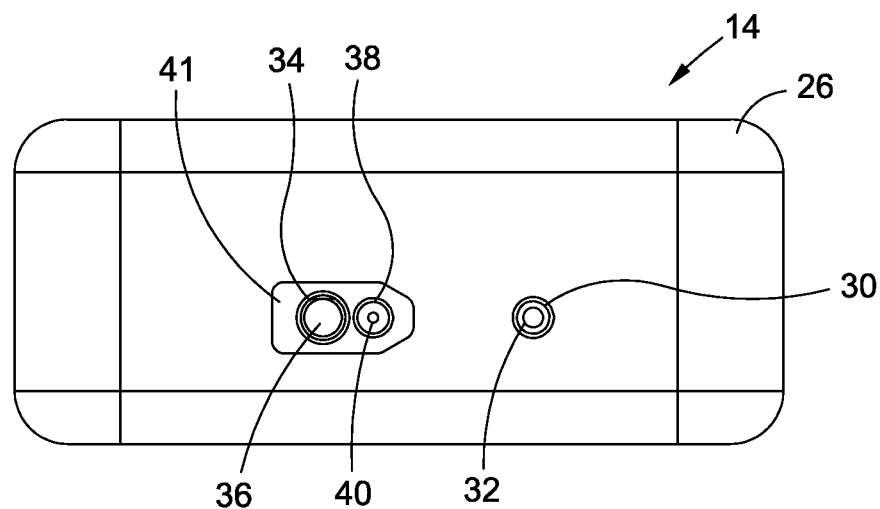
FIG. 8 is a bottom elevational view of the cooling unit shown in FIG. 4.
Figure 9:
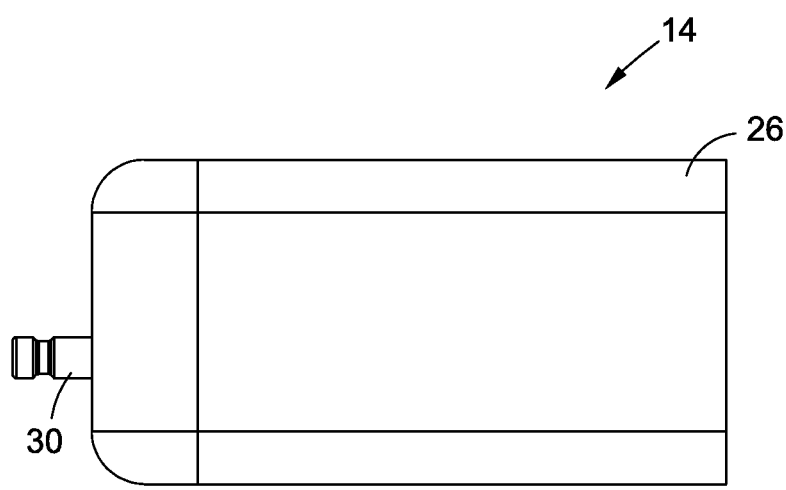
FIG. 9 is a right side elevational view of the cooling unit shown in FIG. 4.

Also included in the cooling unit 14 is an elongate, linear pressure sensing port 38, the majority of the length of which is also disposed within the interior of the housing 26. The pressure sensing port 38 also has a tubular configuration, with one end thereof extending into the receptacle 28, and the opposite end thereof extending to and terminating at that peripheral side surface of the housing 26 having a portion of the gas inlet port 30 protruding therefrom. The pressure sensing port 38 defines a pressure sensing lumen 40 which fluidly communicates with ambient air and with the interior of the receptacle 28 when the cooling unit 14 is not cooperatively engaged to the ventilator 12. As best seen in FIGS. 2, 3 and 8, those ends of the delivery port 34 and pressure sensing port 38 extending to the peripheral side surface of the housing 26 actually terminate at and thus reside within a recess 41 formed within such side surface.

Importantly, in the cooling unit 14, the orientations of the inlet, delivery, and pressure sensing ports 30, 34, 38 relative to the receptacle 28 are selected such that the advancement of that peripheral side surface of the ventilator housing 20 having the inlet, outlet and pressure sensing ports extending thereto into the receptacle 28 will result in the coaxial alignment of that portion of the gas delivery port 34 protruding into receptacle 28 with the outlet port of the ventilator 12, and the coaxial alignment of that portion of the pressure sensing port 38 protruding into the receptacle 28 with the pressure sensing port of the ventilator 12. Similarly, the gas inlet port 30 will be coaxially aligned with the inlet port of the ventilator 12. When the ventilator housing 20 is fully advanced into the receptacle 28, those portions of the delivery and pressure sensing ports 34, 38 protruding into the receptacle 28 are slidably advanced into the outlet and pressure sensing ports, respectively, of the ventilator 12. As a result, the delivery lumen 36 of the delivery port 34 is fluidly coupled to the outlet port of the ventilator 12, with the pressure sensing lumen 40 of the pressure sensing port 38 similarly being fluidly coupled to the pressure sensing port of the ventilator 12. Though no portion of the inlet port 30 is advanced into the inlet port of the ventilator 12, the inlet lumen 32 of the gas inlet port 30 fluidly communicates with the inlet ports of the ventilator 12 by virtue of its coaxial alignment there with, the inlet port of the ventilator 12 being firmly seated against that end of the inlet lumen 32 terminating at the receptacle 28.

As is best seen in FIG. 5, the cooling unit 14 further comprise a thermoelectric cooler 42 which is disposed within the interior of the cooling unit housing 26 proximate the inlet, delivery and pressure sensing ports 30, 34, 38. More particularly, the thermoelectric cooler 42 is disposed within that portion of the interior of the housing 26 disposed between the receptacle 28 and the peripheral side surface having the inlet, delivery and pressure sensing ports 30, 34, 38 extending thereto. The thermoelectric cooler 42 is preferably a Peltier plate or cell 44 disposed between a cooling plate 46 which absorbs heat and a heat sink 48 which dissipates heat. The cooling plate 46 is preferably situated so as to be directly abutted against virtually the entire length of the delivery port 34, except that portion thereof protruding into the interior of the receptacle 28. The cooling plate 46 of the thermoelectric cooler 42 is also abutted against virtually the entire length of the inlet port 30, except for that portion thereof protruding from the housing 26. Still further, the cooling plate 46 is abutted against virtually the entire length of the pressure sensing port 38, except for that portion thereof protruding into the receptacle 28 of the housing 26. An exemplary thermoelectric cooler 42 which is suitable for integration into the cooling unit 14 is produced by TE Technology, Inc.

The cooling unit 14 is further provided with a cooling fan 50 which is also disposed within the interior of the housing 26 and cooperatively engaged to the heat sink 48 of the thermoelectric cooler 42. More particularly, as seen in FIG. 5, the cooling fan 50 is preferably oriented so as to be located directly adjacent the cooling grill 29 of the housing 26. When activated, the cooling fan 50 is operative to circulate air in a manner dissipating the heat generated by the heat sink 48 of the thermoelectric cooler 42 through the cooling grill 29 of the housing 26.

In the cooling unit 14, is, it is contemplated that both the thermoelectric cooler 42 and the cooling fan 50 may be provided with power from a power source 52 which is disposed in the interior of either of the housings 20, 26, or is external thereto. Along these lines, it is also contemplated that such power source 52 may be that used to power other functions of the ventilator 12.

In the ventilation system 10, the patient circuit 16 facilitates the operative coupling of the patient interface 18 to the cooling unit 14, and hence the ventilator 12. In a typical implementation, the patient interface 16 comprises a main delivery tube 54 which is fluidly connectable to the cooling unit 14, and an identically configured pair of first and second ancillary delivery tubes 56, 58 which are fluidly coupled to an extend between the main delivery tube 54 and the patient interface 18. More particularly, one end of each of the first and second ancillary delivery tubes 56, 58 is fluidly coupled to that end of the main delivery tube 54 opposite the end fluidly coupled to the cooling unit 14, with the opposite end of each of the first and second ancillary delivery tubes 56, 58 being fluidly coupled to the patient interface 18.

In the ventilation system 10 shown in FIG. 1, the main delivery tube 54 may comprise a dual-lumen tube defining a gas delivery lumen and a pressure sensing lumen. Similarly, each of the first and second ancillary delivery tubes 56, 58 may comprise a dual-lumen tube. More particularly, the first ancillary delivery tube 56 may define a gas delivery lumen and a pressure sensing lumen, with the second ancillary delivery tube 58 defining a gas delivery lumen and a pilot lumen. The inclusion of the aforementioned pressure sensing and pilot lumens in the first and second ancillary delivery tubes 56, 58, respectively, is contemplated if the ventilation system 10 is outfitted with a patient interface 18 such as a nasal pillows mask including a piloted exhalation valve in accordance with the teachings of Applicant's U.S. patent application Ser. No. 13/784,561 entitled VENTILATION MASK WITH INTEGRATED PILOTED EXHALATION VALVE filed Mar. 4, 2013, the disclosure of which is incorporated herein by reference.

It is contemplated that the main delivery tube 54, as a dual-lumen tube, will be connected to the cooling unit 14 via the insertion of one end portion thereof into the recess 41 such that the gas delivery lumen of the main delivery tube 54 is coaxially with and fluidly coupled to the gas delivery lumen 36 defined by the delivery port 34, and the pressure sensing lumen of the main delivery tube 54 is coaxially aligned with and fluidly coupled to the pressure sensing lumen 40 defined by the pressure sensing port 38. Though not shown with particularity in FIG. 1, the first and second ancillary delivery tubes 56, 58, as dual lumen tubes, are preferably fluidly coupled to the main delivery tube 54 through the use of a Y-connector which is operative to bifurcate the gas delivery lumen of the main delivery tube 54 into the gas delivery lumens of each of the first and second ancillary delivery tubes 56, 58. The Y-connector is further operative to fluidly couple the pressure sensing lumen of the main delivery tube 54 to the pressure sensing lumen of the first ancillary delivery tube 56, and to further fluidly couple the gas delivery lumen of the main delivery tube 54 to the pilot lumen of the second ancillary delivery tube 58. A comprehensive description of a tubing arrangement which may satisfy the patient interface 18 of the ventilation system 10 (including various dual-lumen tubes) is included in Applicant's U.S. patent application Ser. No. 13/798,931 entitled VENTILATION MASK WITH INTEGRATED PILOTED EXHALATION valve filed Mar. 13, 2013, the disclosure of which is also incorporated herein by reference.

In an exemplary sequence of steps for using the ventilation system 10 as outfitted with the patient circuit 16 comprising the main delivery tube 54 and the first and second ancillary delivery tubes 56, 58 described above, the ventilator 12 is initially releasably attached to the cooling unit 14 in the aforementioned manner. Thereafter, that end of the main delivery tube 54 opposite the end fluidly coupled to the first and second ancillary delivery tubes 56, 58 is fluidly coupled to the cooling unit 14 in the matter also described above. The simultaneous activation of the ventilator 12 and the cooling unit 14 facilitates the flow of a pressurized therapeutic gas (e.g., air) from the outlet port of the ventilator 12 into the gas delivery lumen 36 defined by the gas delivery port 34 of the cooling unit 14. The serpentine configuration of the gas delivery port 34, coupled with its direct abutment against the cooling plate 46 of the thermoelectric cooler 42, facilitates a substantial reduction in the temperature of the gas flowing through the delivery lumen 36. From the delivery lumen 36, the pressurized gas flows into and through the gas delivery lumen of the main delivery tube 54, and thereafter bifurcated in the aforementioned manner into each of the gas delivery lumens of the first and second ancillary delivery tubes 56, 58. The cooled gas thereafter flows from the gas delivery lumens of the ancillary first and second delivery tubes 56, 58 into the patient interface 18, and ultimately into the lungs of a patient wearing the same.

Figure 7A:
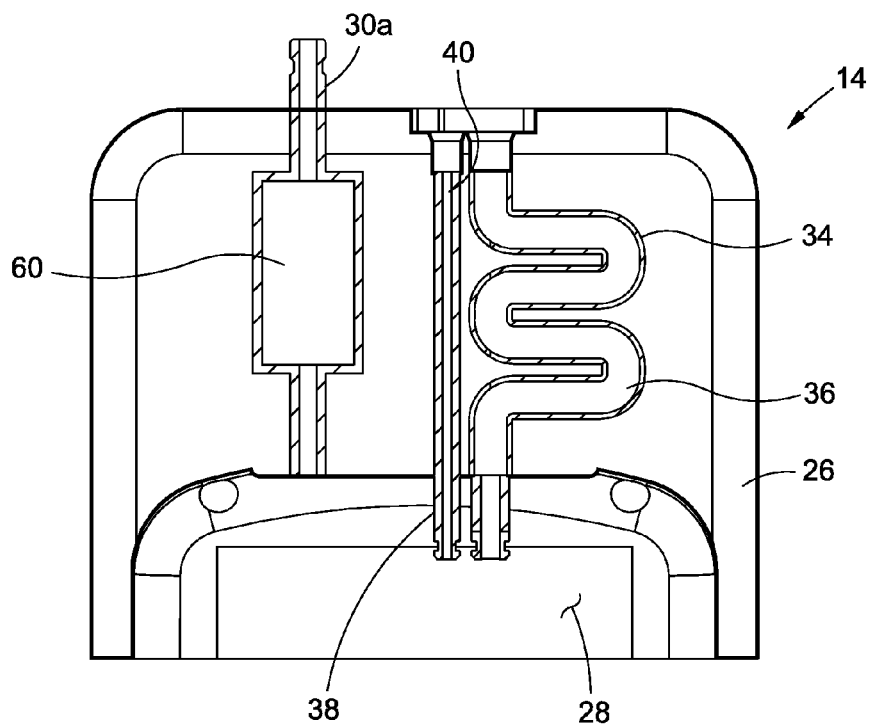
FIG. 7A is a cross-sectional view similar to FIG. 7, but depicting a minor variation of the cooling unit of the present invention.

In the aforementioned ventilation system 10, air, air with oxygen, heliox, or another breathable gas is drawn into the inlet port of the ventilator 12 via the inlet lumen 32 defined by the inlet port 30 of the cooling unit 14. Because, like the pressure sensing port 38, the inlet port 30 is abutted directly against the cooling plate 46 of the thermoelectric cooler 42, some measure of pre-cooling of the gas entering the inlet port of the ventilator 12 occurs prior to the same being pressurized and channeled into the delivery lumen 36 of the delivery port 34 via the outlet port of the ventilator 12. Along these lines, FIG. 7A depicts a potential variant of the gas inlet port 30 which may be integrated into the cooling unit 14 in accordance with the present invention. This alternative gas inlet port 30a varies from the aforementioned gas delivery port 30 by virtue of its inclusion of an enlarged gas cooling chamber 60 approximately midway between the opposed ends thereof. The gas cooling chamber 60 of the delivery port 30a, which will normally be pressurized during the concurrent operation of the ventilator 12 and cooling unit 14 including the same, facilitates a higher threshold of pre-cooling of the gas or air drawn into and through the delivery port 30a into the ventilator 12 in comparison to the level of pre-cooling achieved with the inlet port 30 not including the gas cooling chamber 60. Though not shown, it is also contemplated that a greater level of pre-cooling of the air or other breathable gas may be achieved by forming the inlet port 30 to have a serpentine configuration similar to that of the delivery port 34. Such serpentine inlet port 30 could be outfitted with the aforementioned gas cooling chamber as well, as could the delivery port 34.

In the ventilation system 10 wherein the cooling unit 14 is operatively coupled to the ventilator 12 in the aforementioned manner, the pressure sensing lumen defined by the first ancillary delivery tube 56 is fluidly coupled to the pressure sensing port of the ventilator 12 via the pressure sensing lumen of the main delivery tube 54 and the pressure sensing lumen 40 defined by the pressure sensing port 38 of the cooling unit 14. Importantly, the pressure sensing line collectively defined by the pressure sensing lumen 40 and the pressure sensing lumens of the main and first ancillary delivery tubes 54, 56 is uninterrupted, and fluidly isolated from both the inlet port 30, the delivery port 34, and the gas delivery lumens of the main delivery and as the first ancillary delivery tubes 54, 56.

Referring now to FIGS. 10-14, in the above-described ventilation system 10, there is a potential for the therapeutic benefits provided by the cooling of the therapeutic gas to be reduced by the warming of such gas which occurs as a result of its travel or flow from the cooling unit 14 through the main delivery tube 54 and first and second ancillary delivery tubes 56, 58 of the patient interface 18. To combat such potential warming, it is contemplated that a cooling unit 14*a* may be used in the ventilation system 10 as an alternative to the above-described cooling unit 14. The cooling units 14, 14*a* are substantially similar to each other, with only the differences therein being highlighted below.

Figure 10:
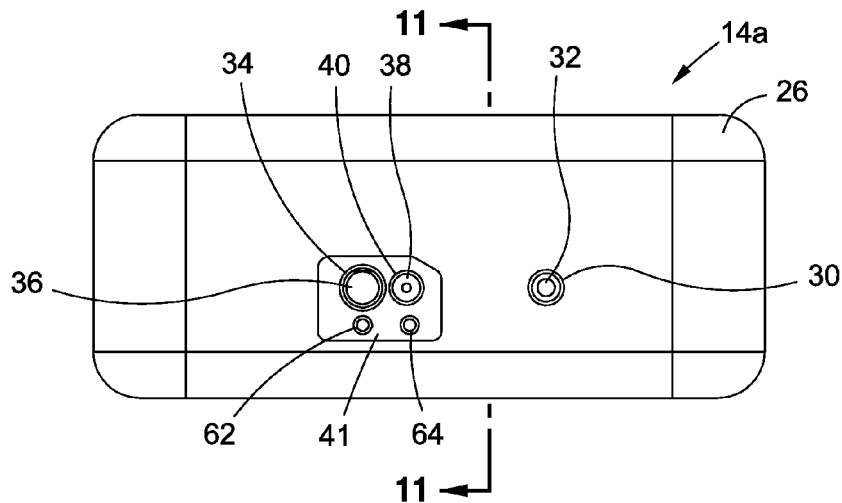
FIG. 10 is a bottom elevational view similar to FIG. 8, but depicting an alternative embodiment of the cooling unit of the present invention.
Figure 11:
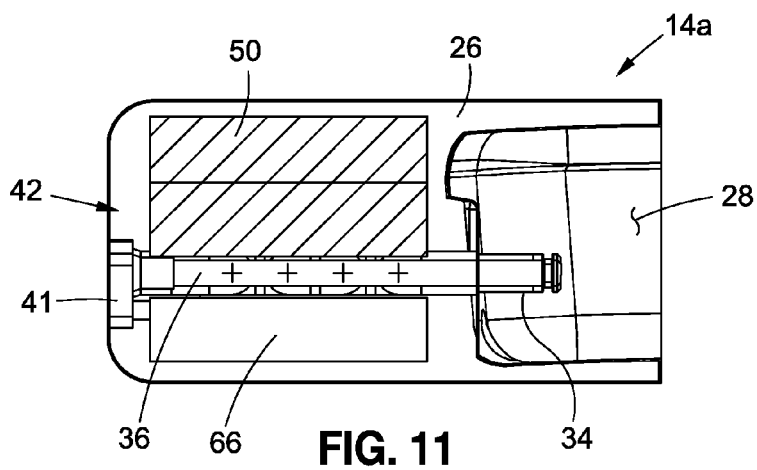
FIG. 11 is a cross-sectional view taken along line 11-11 of F FIG. 10.

The distinction between the cooling units 14, 14*a* lies in the further inclusion of a cooling fluid circulation system for the patient interface 16 in the cooling unit 14*a*. Such circulation system comprises a cooling fluid send port 62 and a cooling fluid return port 64. As best seen in FIG. 10, the send port 62 is located within the recess 41 immediately below the gas delivery port 34. Similarly, the return port 64 is disposed within the recess 41 immediately below the pressure sensing port 38. As is seen in FIG. 11, the send and return ports 62, 64 are each fluidly coupled to a cooling fluid circulation pump 66 of the circulation system which is disposed within the housing 26 of the cooling unit 14*a*. The circulation pump 66 is located directly adjacent the delivery port 34, which is thus disposed between the circulation pump 66 and the thermoelectric cooler 42. Due to its location within the housing 26, the circulation pump 66, and hence any fluid circulated therethrough, is effectively cooled by the cooling plate 46 of the thermoelectric cooler 42. Like the thermoelectric cooler 42 and the cooling fan 50, it is contemplated that the circulation pump 66 of the cooling unit 14*a* will be electrically connected to and thus powered by the aforementioned power source 52.

Figures 12, 13:
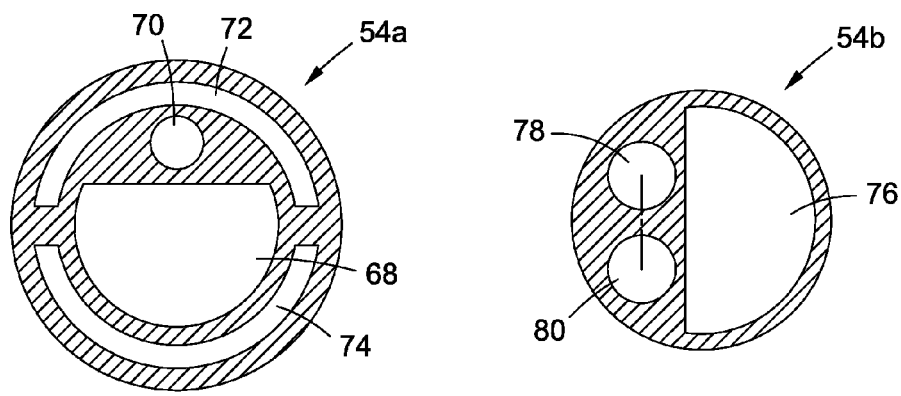
FIG. 12 is a cross-sectional view of an exemplary multi-lumen to which may be used in conjunction with the embodiment of the cooling unit shown in FIGS. 10 and 11.
FIG. 13 is a cross-sectional view of alternative multi-lumen tube which may be used in conjunction with a slight variation of the cooling unit shown in FIGS. 10 and 11.

In a ventilation system 10 including the cooling unit 14*a* as an alternative to the aforementioned cooling unit 14, the main delivery tube 54 comprising the above-described dual-lumen or bi-lumen tube is preferably substituted with an alternative main delivery tube 54*a* comprising the quad-lumen tube shown in FIG. 12. The main delivery tube 54*a*, as a quad-lumen tube, defines a gas delivery lumen 68 analogous to the gas delivery to lumen of the dual-lumen version of the above-described main delivery tube 54, and a pressure sensing lumen 70 analogous to the pressure sensing lumen of the dual-lumen version of such main delivery tube 54. However, in addition to the gas delivery and pressure sensing lumens 68, 70, the quad-lumen version of the main delivery tube 54*a* further defines a cooling fluid send lumen 72 and a cooling fluid return lumen 74. The main delivery tube 54*a* has a generally circular cross-sectional configuration, with the send and return lumens 72, 74 thereof each having a generally U-shaped, semi-circular configuration. As a result, the send and return lumens 72, 74 each span a collective circumference of approximately 360°.

In the ventilation system 10 including the cooling unit 14*a*, one end portion of the main delivery tube 54*a* is fluidly coupled to the cooling unit 14*a*. More particularly, that end portion of the main delivery tube 54*a* opposite the end fluidly coupled to the first and second ancillary delivery tubes 56, 58 is advanced into the recess 41 such that the gas delivery lumen 68 of the main delivery tube 54*a* is fluidly coupled to the gas delivery lumen 36 defined by the gas delivery port 34, and the pressure sensing lumen 70 of the main delivery tube 54*a* is fluidly coupled to the pressure sensing lumen 40 defined by the pressure sensing port 38. At the same time, the send lumen 72 of the main delivery tube 54*a* is fluidly coupled to the send port 62 of the cooling unit 14*a*, with the return lumen 74 of the main delivery tube 54*a* being fluidly coupled to the return port 64 of the cooling unit 14*a*. In this regard, the activation of the circulation pump 66 is operative to facilitate the flow of a cooling fluid through the send and return lumens 72, 74 of the main delivery tube 54*a* via the send and return ports 62, 64 of the cooling unit 14*a* in a closed loop system. It is contemplated that such cooling fluid may either be a gas coolant or a liquid coolant. If a gas coolant is used as the cooling fluid, it is further contemplated that the source of such gas coolant may be directly from the delivery port 34 of the cooling unit 14*a* through the placement of the send port 62 into fluid communication therewith such that the cooling fluid is the same breathable gas being delivered by the gas delivery lumen 68. Alternatively, the source of the gas coolant may be ambient air by outfitting the send port 62 with an ambient air inlet. If the cooling fluid is a liquid coolant, it is contemplated that the circulation pump 66, and hence the send and return ports 62, 64 and send and return lumens 72, 74, will be placed into fluid communication with a suitable coolant liquid reservoir disposed within either of the housings 20, 26, or alternatively located externally relative thereto.

Referring now to FIG. 13, it is further contemplated that a variant of the cooling unit 14*a* may be provided wherein the aforementioned return port 64 is omitted therefrom. In this instance, it is further contemplated that the main delivery tube 54*a* comprising the above-describe quad-lumen tube will be substituted with a further alternative main delivery tube 54*b* comprising the tri-lumen tube shown in FIG. 13. The main delivery tube 54*b*, as a tri-lumen tube, defines a gas delivery lumen 76 analogous to the gas delivery lumen 68 of the main delivery tube 54*a*, a pressure sensing lumen 78 analogous to the pressure sensing lumen 70 of the main delivery tube 54*a*, and a send lumen 80 analogous to the send lumen 72 of the main delivery tube 54*a*.

In the ventilation system 10 including the aforementioned variant of the cooling unit 14*a*, one end portion of the main delivery tube 54*b* is fluidly coupled to the cooling unit 14*a*. More particularly, that end portion of the main delivery tube 54*b* opposite the end fluidly coupled to the first and second ancillary delivery tubes 56, 58 is advanced into the recess 41 such that the gas delivery lumen 76 of the main delivery tube 54*b* is fluidly coupled to the gas delivery lumen 36 defined by the gas delivery port 34, and the pressure sensing lumen 78 of the main delivery tube 54*b* is fluidly coupled to the pressure sensing lumen 40 defined by the pressure sensing port 38. At the same time, the send lumen 80 of the main delivery tube 54*b* is fluidly coupled to the send port 62 of the cooling unit 14*a*. In this regard, the activation of the circulation pump 66 is operative to facilitate the flow of a cooling fluid through the send lumen 80 of the main delivery tube 54*b* via the send port 62 of the cooling unit 14*a*. It is contemplated that such cooling fluid will exclusively be a gas coolant, the source of which may be directly from the delivery port 34 of the cooling unit 14*a* through the placement of the send port 62 into fluid communication therewith, or by alternatively further outfitting the send port 62 with an ambient air inlet. Along these lines, it is contemplated that the cooling fluid circulated unidirectionally through the send lumen 80 may be bled back into the pressured gas flow to the patient interface 18 either at the Y-connector integrated into the patient circuit 16 or at the patient interface 18. If the patient interface 18 is a nasal interface such as a nasal pillows mask as described in the '856 Application identified above, the patient circuit 16 may further include a flow channel or conduit that terminates prior to an end of the patient circuit 16 or at the patient interface, in order to create a jet venturi of the ventilation gas, thereby entraining ambient air in the patient circuit 16 and minimizing leakage therefrom.

Figure 14:
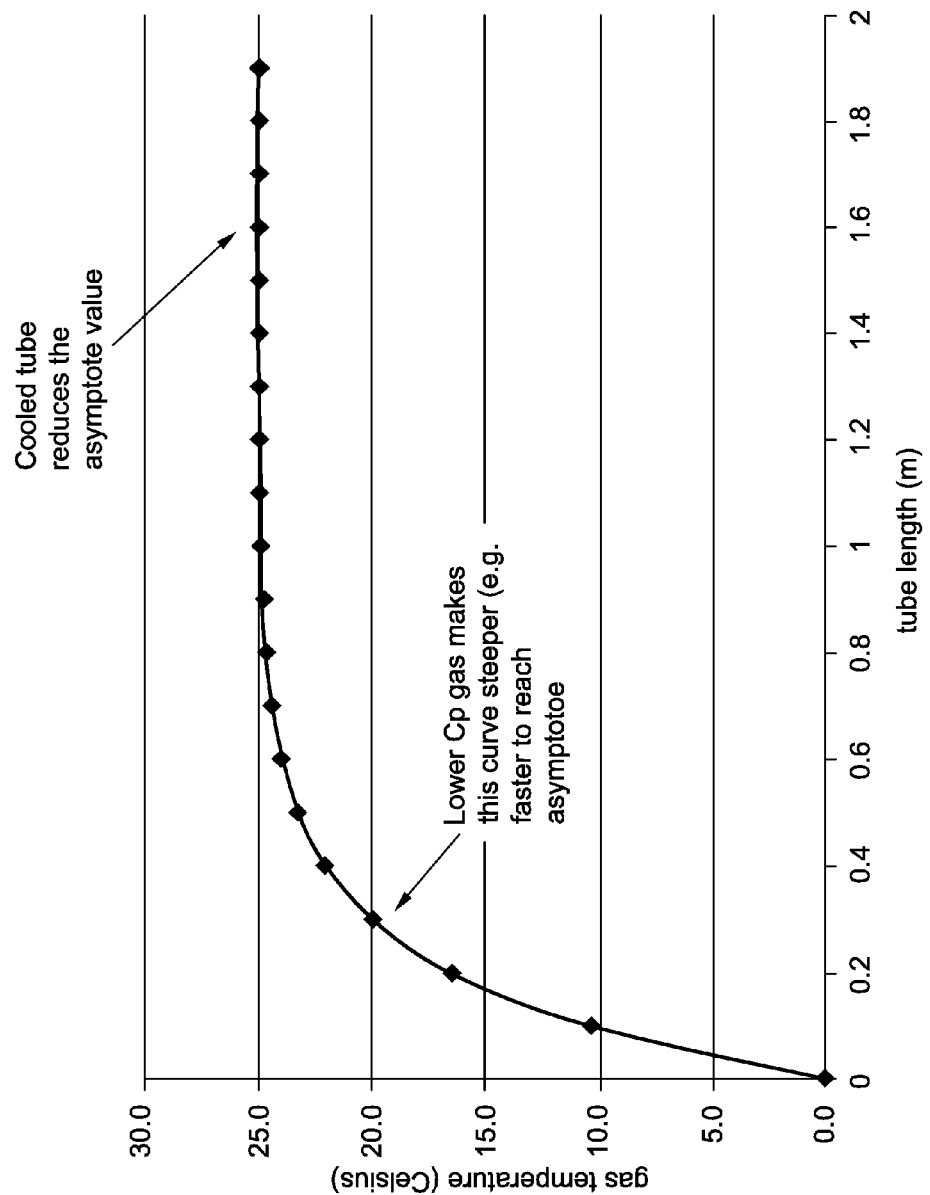
FIG. 14 is a graphical representation indicative of the functionality of a delivery tube cooling system which may be integrated into the cooling unit and used in conjunction with either of the multi-lumen tubes shown in FIGS. 12 and 13.

The efficacy of either iteration of the cooling fluid circulation system described above in maintaining the temperature of a gas circulated through the patient circuit 16 at reduced levels is graphically depicted in FIG. 14.

In the ventilation system 10, it is further contemplated that the cooling unit 14, 14*a* may be placed into electrical communication with the ventilator 12, with the functionality of the cooling unit 14, 14*a* being governed by control signals received from the ventilator 12. These control signals may be derived from user inputs into the ventilator 12. In addition or as an alternative, the control signals may be derived from feedback transmitted to the ventilator 12 or directly to the control unit 14, 14*a* from one or more sensors integrated into prescribed locations within the patient circuit 16 and/or patient interface 18. By way of example and not by way of limitation, the control of the cooling unit 14, 14*a* may be based on, among other things, the sensed temperature of the breathable gas at the patient interface 18 and/or the inlet port 30, the length of the main delivery tube 54, 54*a* of the patient circuit 16, the flow rate of breathable gas produced at the outlet port or f the ventilator 12, etc.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. A ventilation gas cooling unit operative to cool a pressurized fluid generated by a ventilator having an inlet and an outlet, the cooling unit comprising:
 a housing;
 an inlet port at least partially disposed within the housing, the inlet port having an inlet port external end and an inlet port internal end, the inlet port being fluidly connectible to a source of therapeutic breathing gas at the inlet port external end and fluidly connectible to the inlet of the ventilator at the inlet port internal end;
 a delivery port at least partially disposed within the housing, the delivery port having a delivery port external end and a delivery port internal end, the delivery port being fluidly connectible to a patient circuit at the delivery port external end and fluidly connectable to the outlet of the ventilator at the delivery port internal end; and
 a thermoelectric cooler disposed within the housing and comprising a Peltier plate disposed between a cooling plate and a heat sink;
 wherein the cooling plate of the thermoelectric cooler is positioned adjacent to the portion of the delivery port disposed within the housing and the portion of the inlet port disposed within the housing, and is operative to cool fluid flowing through the delivery port and to cool fluid flowing through the inlet port; and
 wherein the cooling unit has a modular configuration adapted for releasable, retrofit attachment to the ventilator.

2. The ventilation gas cooling unit of claim 1 further comprising a cooling unit pressure sensing port at least partially disposed within the housing, the cooling unit pressure sensing port having a cooling unit pressure sensing port internal end and a cooling unit pressure sensing port external end, the cooling unit pressure sensing port being fluidly connectible to the patient circuit at the cooling unit pressure sensing port external end and fluidly connectable to a ventilator pressure sensing port of the ventilator outlet at the cooling unit pressure sensing port internal end.

3. The ventilation gas cooling unit of claim 2, wherein the cooling plate of the thermoelectric cooler is additionally positioned adjacent to the portion of the cooling unit pressure sensing port disposed within the housing, and is operative to cool fluid flowing through the cooling unit pressure sensing port.

4. The ventilation gas cooling unit of claim 1 wherein the housing of the cooling unit defines a receptacle sized and configured to accommodate a portion of the ventilator.

5. The ventilation gas cooling unit of claim 1 further comprising a cooling fan disposed within the housing adjacent the heat sink of the thermoelectric cooler.

6. The ventilation gas cooling unit of claim 5 wherein the housing of the cooling unit defines a cooling grill adjacent to and in fluid communication with the cooling fan.

7. The ventilation gas cooling unit of claim 1 wherein the inlet port further comprises a pressurized cooling chamber.

8. The ventilation gas cooling unit of claim 1 wherein the delivery port follows a serpentine pattern.

9. The ventilation gas cooling unit of claim 1 further comprising a cooling fluid send port fluidly connectible to a cooling fluid send lumen of the patient circuit.

10. The ventilation gas cooling unit of claim 9 wherein the cooling fluid send port is in fluid communication with the delivery port.

11. The ventilation gas cooling unit of claim 9 wherein the cooling fluid send port comprises an ambient air inlet.

12. The ventilation gas cooling unit of claim 9 further comprising a cooling fluid pump which is disposed within the housing adjacent to the cooling plate, the pump being fluidly coupled to the cooling fluid send port and operative to selectively facilitate flow of a cooling fluid through the cooling fluid send port and the cooling fluid send lumen of the patient circuit.

13. The ventilation gas cooling unit of claim 12 further comprising a cooling fluid return port fluidly connectable to a cooling fluid return lumen of the patient circuit, the pump further being fluidly coupled to the cooling fluid return port and operative to selectively facilitate flow of the cooling fluid through the cooling fluid send lumen and the cooling fluid return lumen of the patient circuit via the cooling fluid send port and cooling fluid return port of the cooling unit in a closed loop system.

14. The ventilation gas cooling unit of claim 13 wherein the cooling fluid is a gas coolant.

15. The ventilation gas cooling unit of claim 13 wherein the cooling fluid is a liquid coolant.

* * * * *